United States Patent [19]

Mizushima et al.

[11] Patent Number: 4,929,559
[45] Date of Patent: May 29, 1990

[54] DNA CONTAINING THE PROLIPOPROTEIN SIGNAL PEPTIDASE GENE

[75] Inventors: Shoji Mizushima; Hideo Yamagata, both of Nagoya, Japan

[73] Assignee: Sankyo Company Limited, Tokyo, Japan

[21] Appl. No.: 161,414

[22] Filed: Feb. 23, 1988

Related U.S. Application Data

[63] Continuation of Ser. No. 634,441, Jul. 25, 1984.

[30] Foreign Application Priority Data

Sep. 27, 1983 [JP] Japan .................. 58-179046

[51] Int. Cl.[5] .................. C12N 1/20; C12N 15/00; C07H 15/12
[52] U.S. Cl. .................. 435/252.33; 435/172.3; 435/212; 435/220; 435/252.3; 435/320; 435/849; 536/27; 935/14; 935/29; 935/72; 935/73
[58] Field of Search ............ 435/172.3, 252.3, 252.33, 435/320; 536/27; 935/14, 29, 73, 72

[56] References Cited

PUBLICATIONS

Silver et al., *J. Bacteriol.*, 154(2):569–572, 1983 (May).
Tokienaga et al., *J. of Biol. Chem.* 258(20):12102–12105, 1983 (Oct.).
Regue et al., *J. of Bacteriol.* 158(2):632–635, 1984 (May).
Clark et al., *Cell* 9:91–99 (1976).
Yamagata et al., *FEBS Letters* 158(2):301–304, 1983 (July 25).
H. Yamagata, N. Taguchi, K. Daishima, S. Mizushima, Mol. Gen. Genet. 192(10), (1983).
H. Yamada, M. Kitagawa, M. Kawakami, S. Mizushima, FEBS Lett. 171(245), (1984).
F. Yu, H. Yamada, K. Daishima, S. Mizushima, FEBS Lett. 173(264), (1984).
H. Yamada, H. Yamagata, S. Mizushima, FEBS Lett. 166(179), (1984).
P. Silver, W. Wickner, J. Bacteriol 154(569), (1983).
T. Date, W. Wickner, Proc. Natl. Acad. Sci. USA 78 (6106), (1981).
N. J. Dibb, P. B. Wolfe, J. Bacteriol. 166(83), (1986).
P. B. Wolfe, W. Wickner, J. M. Goodman, J. Biol. Chem. 258(12073), (1983).
C. Watts, W. Wickner, J. Biol. Chem. 255(7973), (1980).

Primary Examiner—Thomas D. Mays
Attorney, Agent, or Firm—Frishauf, Holtz, Goodman & Woodward

[57] ABSTRACT

One of the *E. coli* strains of the Clarke and Carbon collection [Cell, 9, 91–99] has been found to contain a plasmid which we have isolated and termed pLC3-13, which contains genetic information coding for prolipoprotein signal peptidase. A 4.3 kb fragment containing this genetic information has been prepared, other plasmids have been prepared containing at least this fragment and strains of *E. coli* have been transformed thereby.

15 Claims, 3 Drawing Sheets

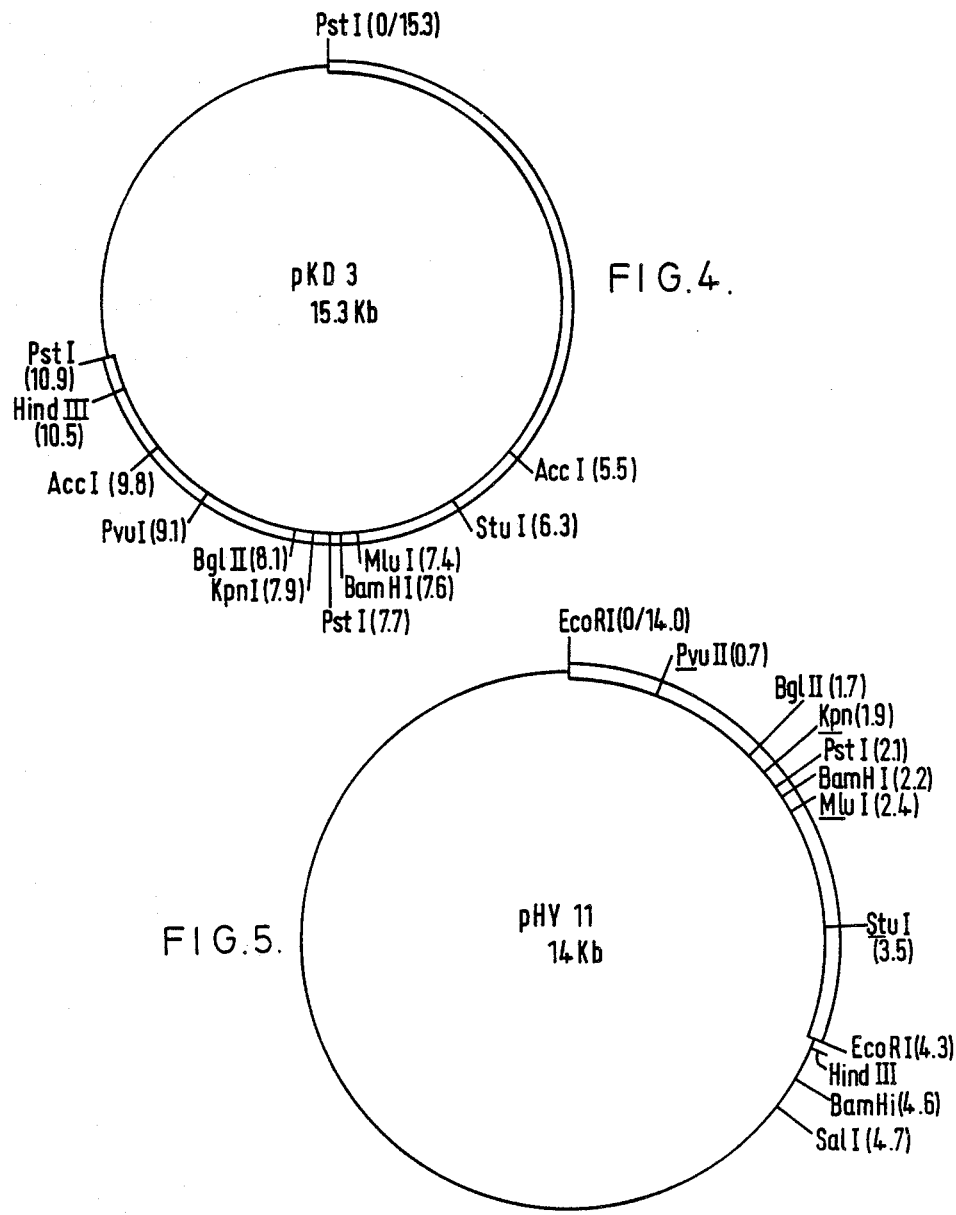

DNA CONTAINING THE PROLIPOPROTEIN SIGNAL PEPTIDASE GENE

This application is a continuation, of application Ser. No. 634,441, filed July 25, 1984.

BACKGROUND TO THE INVENTION

The present invention relates to DNA containing the prolipoprotein (PLP) signal peptidase gene, to isolation of such DNA from appropriate strains of *Escherichia coli* (hereinafter "*E. coli* "). to plasmids incorporating such DNA and to microorganisms transformed with said plasmids.

It is generally considered that many microorganisms. including *E. coli*, produce at least some of their proteins initially in the form of a precursor. This applies particularly to outer cell wall and periplasmic proteins. Such a precursor can comprise the desired protein attached, for example at its amino-terminus, to a signal peptide, signal peptidases, which cleave off such a signal peptide, are considered to play a key role in the process of protein secretion across the cytoplasmic membrane. Among the *E. coli* proteins, the major outer membrane lipoprotein (LP) is the most abundant in terms of the number of molecules and has many unique features. It is believed that the structural gene for lipoprotein in *E. coli* can be transcribed highly efficiently and have been made to use lipoprotein as an expressionn vector.

However, to date, there are relatively few cases where such an expression vector has been successfully used to produce large quantities of proteins. This is probably because these proteins are toxic to *E. coli* and either kill the *E. coli* cells or are degraded when the concentration exceeds a certain (low) level. The LP gene is structural and it might be thought that increasing the number of such genes in the microbial cell would lead to an increase in the protein product. However, even when cloned into a multi-copy plasmid, such as PBR322, successful expression of large quantities to the desired protein does not seem to be achieved. It is probable that this is because the prolipoprotein produced by expression of the Lp genes in large quantities kills the cells.

This problem could be overcome by causing the gene products to be secreted outside of the cytoplasm, namely in the periplasm or in a medium. If such products can be secreted outside the cytoplasm away from the metabolic system of the cell, even a protein harmful to the metabolism can be produced and decomposition of the desired proteins in the cell will not occur. An important element in such secretion is the PLP signal peptidase. If the quantity of PLP signal peptidase produced is not commensurate with the quantity of PLP or of PLP linked to another desired prorein, then the quantity of PLP in the cell will increase, thus leading to poisoning of the cell.

A means of increasing production of PLP signal peptidase is thus urgently needed in order to enable genetically engineered cells, particularly *E. coli* cells, to produce large quantities of other desirable proteins. Moreover, excretion of desired proteins outside the cytoplasm has another advantage. When producing proteins by fermentation, isolation and purification of the protein product is far easier and more efficient if the product is outside the cell, particularly in the culture medium, than it is if the protein product remains within the cell.

We have now successfully isolated a DNA segment coding for PLP signal peptidase from the chromasomal material of *E. coli* and have incorporated the segment into a plasmid and demonstrated successful expression of the desired signal peptidase when the resulting plasmid is introduced into a microorganism.

BRIEF SUMMARY OF INVENTION

Accordingly, in its broadest aspect, the present invention provides a DNA sequence coding for the prolipoprotein signal peptidase of *E. coli* and removed from its native *E. coli* chromasome.

The invention also provides a method of producing such a DNA sequence and various means whereby such a sequence may be utilized.

BRIEF DESCRIpTION OF THE DRAWINGS

In the accompanying drawings:

FIG. 3 shows a restriction enzyme map of a 4.3kb (kilobase pairs) DNA fragment containing the gene coding for PLP signal peptidase and formed by digestion of plasmid pLC3-13 with AccI;

FIG. 4 shows a restriction enzyme map of the recombinant plasmid pKD3;

FIG. 5 shows a restriction enzyme map of the recombinant plasmid pHY11;

DETAILED DESCRIPTION OF INVENTION

Figure 1:
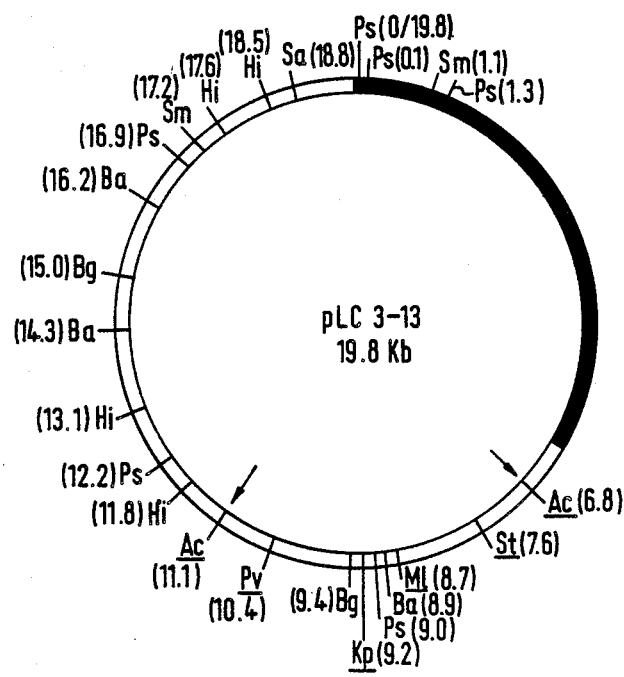
FIG. 1 shows a restriction enzyme map of the plasmid pLC3-13.

We have produced a new plasmid, which we have named pLC3-13, which comprises 19.8 kb and which we have shown to contain a DNA segment of about 4.3 kb containing the gene coding for PLP signal peptidase. The plasmid pLC3-13 is characterized by the restriction enzyme map shown in FIG. 1 of the accompanying drawings. In the FIG.: Ba shows the point of cleavage by the restriction enzyme BamHI; Hi shows the point of cleavage by the restriction enzyme HindIII; ps shows the point of cleavage by pstI; Sa shows the point of cleavage by SalI; Sm shows the point of cleavage by SmaI; Bg shows the point of cleavage by BglII; Kp shows the point of cleavage by KpmI; Ml shows the point of cleavage by MluI; pv Shows the point of cleavage by pvuII; St shows the point of cleavaqe by StuI; and Ac shows the point of cleavage by AccI. The numerals in the FIG. show the positions of cleavage by the respective enzymes in kilobase pairs, setting the position of cleavage by PstI at the twelve o'clock position as the origin of the coordinates. The abbreviations and numerals have a similar meaning in the other FIGS. showing restriction enzyme maps. A strain of *E. coli* (known as *E. coli* strain SANK 71983) incorporating the plasmid pLC3-13 has been deposited with the Fermentation Research Institute, Agency of Industrial Science and Technology, Ministry of International Trade and Industry, Japan, whence it is available under the Accession No. FERM4-p7150.

Other novel plasmids produced in accordance with the invention and containing a gene coding for PLP signal peptidase are as follows:

plasmid pKD3 which is characterized by the restriction enzyme map shown in FIG. 4. This contains about 15.3 kB and is shown in the FIG. with the pstI cleavage point at twelve o'clock as the origin of coordinates. A strain of *E. coli* containing this plasmid has been deposited at said Fermentation Research Institute under the Accession No. FERM-P7151 (*E. coli* SANK 72083).

Plasmid pHY11 is characterized by the restriction enzyme map shown in FIG. 5, in which the cleavage point of EcoRI is shown at the twelve o'clock position as the origin of coordinates. The plasmid contains about 14 kB and a strain of *E. coli* containing the plasmid has been deposited at said Fermentation Research Institute under the Accession No. FERM-P7152 (*E. coli* strain SANK 72183)

Figure 6:
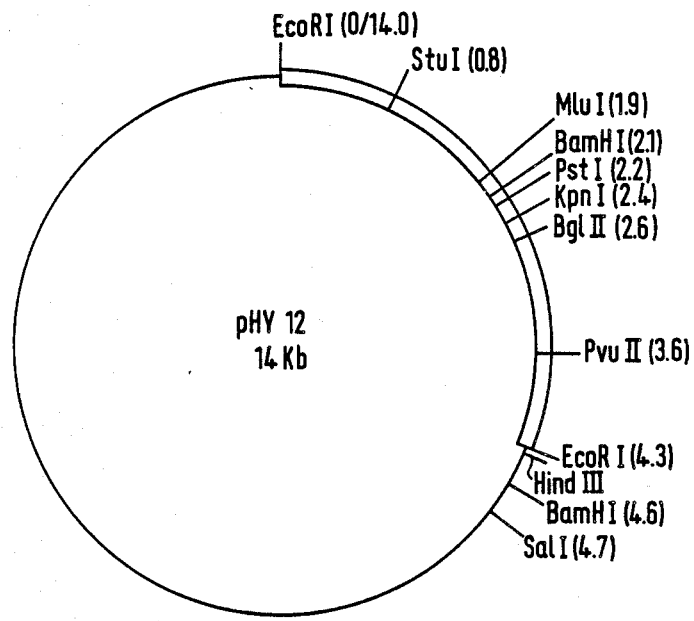
FIG. 6 shows a restriction enzyme map of the recombinant plasmid pHY12.

Plasmid pHY12 is characterized by the restriction enzyme map shown in FIG. 6. in which the cleavage point of EcoRI is shown at the twelve o'clock position as the origin of coordinates. It also contains about 14 kB and was deposited at said Fermentation Research Institute under the Accession No. FERM-P7153 (*E. coli* strain SANK 72283).

Figure 7:
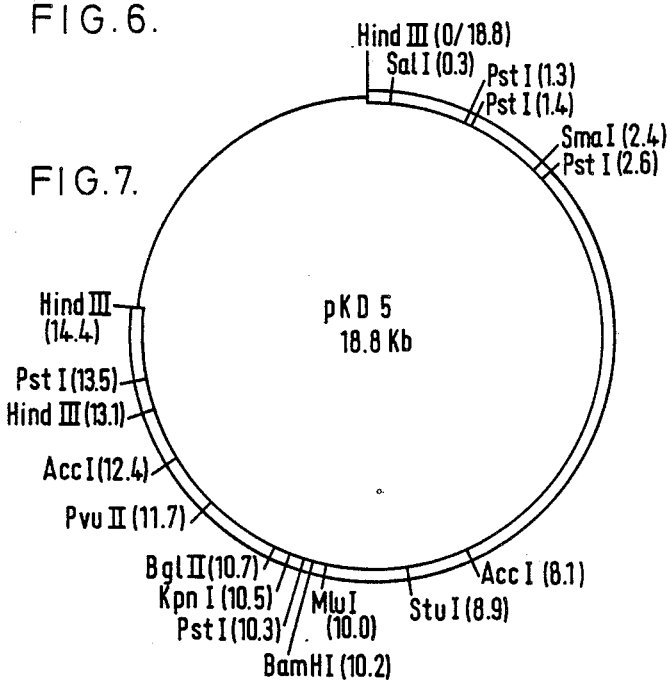
FIG. 7 shows a restriction enzyme map of the recombinant plasmid pKD5.

Plasmid pKD5 is characterized by the restriction enzyme map shown in FIG. 7, in which the HindIII cleavage point is shown at the twelve o'clock position as the origin of coordinates. It contains about 18.8 kB and a strain of *E. coli* containing this plasmid was deposited at said Fermentation Research Institute under the Accession No. FERM-P7151 (*E. coli* strain SANK 72383).

The strain of *E. coli* into which plasmids pKD3, pKD5. pHY11 and pHY12 were introduced for the deposits described above is *E. coli* strain Y8 [H. Yamagata et al., J. Bacteriol. 152, 1163-8 (1982)].

In order to produce a plasmid containing the DNA segment coding for PLP signal peptidase, we screened the 2,000 *E. coli* strains of the Clarke and Carbon collection [Cell, 9,91-99 (1976)]. The screening was effected using an *E. coli* murant, Y815, that has a temperature-sensitive signal pertidase for PLP [Yamagata at et al., J. Bacteriol., 152, 1163-1168 (1982)]. This *E. coli* strain Y815 was deposited at the aforementioned Fermentation Research Institute, whence it is available under the Accession No. FERM-P7686. Strain Y815 is sensitive to isopropyl-β-D-thio-galacropyranoside (IPTG). IPTG promotes the production of prolipoprotein. PLP, and eventually the accumulation of PLP within the cell membrane inhibits growth of the microorganism. This accumulation of PLP in the strain Y815 can be used to detect the presence of a plasmid containing a gene coding for PLP signal peptidase by mixing a sample of the strain under investigation with the strain Y815. If the strain under investigation contains the desired gene, conjugation can lead to the ger.e appearing as a plasmid in the Y815 strain, this will induce the production of extra PLP signal peptidase and the Y815 strain will apparently change from IPTG sensitive to IPTG-insensitive. As described hereinafter in more detail in the Examples, this was carried out with the 2,000 strains of Clarke and Carbon and the requisite strain was selected.

The strain in question was *E. coli* strain SANK 71983 (FERM-P7150). The plasmid pLC3-13, described above, was separated from the strain as described in Example 2.

Location of the DNA segment containing the gene coding for PLP was investigated and other useful plasmids were produced by digesting the purified plasmid pLC3-13 with the restriction enzymes BamHI, HindIII, pstI and BglII; the digested plasmid was then mixed with plasmid pBR322 (which had been digested with the same restriction enzymes) and the fragments were caused to link by T4 DNA ligase.

Using the resulting samples, oli strains Y815 and Y8 were transformed and examined to detect plasmids. 8 novel plasmids. pKD1, pKD2, pKD3, pKD4, pKD5, pKD6, pKD7 and pKD8. containing DNA fragments from the plasmid pLC3-13. were obtained.

Moreover, sub-cloned novel plasmids pHY11 and pHY12 were obtained by digesting pLC3-13 with the restriction enzyme AccI. separating out the 1.3kb fragment and inserting this fragment, with the aid of EcoRI linker into the EcoRI site of plasmid pHY001.

The membrane fractions of *E. coli* strains Y815 and Y8 transformed by these plasmids were measured according to the method of measuring in vitro PLP signal peptidase at a high temperature (60° C) of H. Yamagata [J. Biochem., 93, 1509–1515 (1983)].

Figure 2:
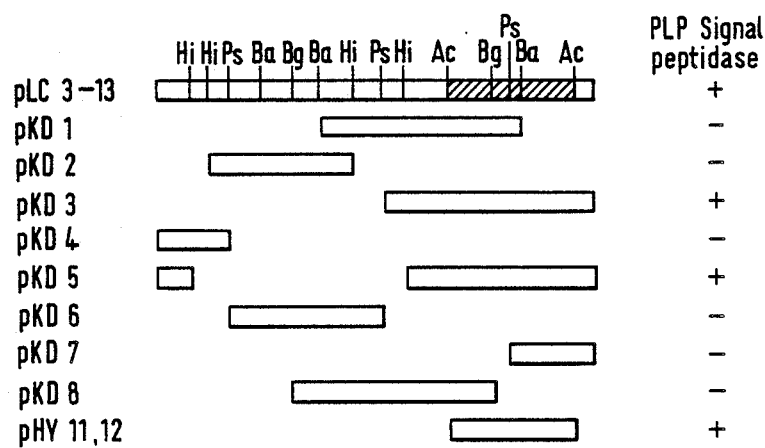
FIG. 2 shows the site of the PLP signal peptidase gene on the plasmid pLC3-13 and the relationship of plasmid pLC3-13 to plasmids pKD1-pKD8, pHY11 and pHY12.

The results obtained are summarized in FIG. 2 of the accompanying drawings, which shows for all of the new plasmids that part of their genetic material which was derived from the chromosomal DNA of *E. coli*. It can be seen that PLP signal peptidase activity was detected in all of those strains transformed by plasmids containing the 4.3 kb fragment characteristic of plasmids pHY11 and pHY12. but that no such activity was detected in strains transformed with plasmids containing only part or none of this segment. Specifically. PLP signal peptidase activity was detected in the strains transformed with plasmids pKD3, pKD5, pHY11 and pHY12. This 4.3 kb DNA fragment is characterized by the restriction enzyme map shown in FIG. 3 of the accompanying drawings and it can be seen from FIGS. 4, 5, 6 and 7, being the restriction enzyme maps of pKD3, pHY11, pHY12 and pKD5, respectively, that these plasmids all contain that fragment; the plasmids pHY11 and pHY12 are identical, except that the fragment has been inserted one way into plasmid pHYOO1 to form plasmid pHY11 and the other way to form plasmid pHY12.

The invention is further illustrated by the following Examples.

EXAMPLE 1

Screening of a strain having a gene complementing the IPTG sensitivity of the mutant strain Y8I5.

*E. coli* of the 2,000 strains of Clarke and Carbon [Cell. 9, 91–99 (1976)]were each inoculated into 0.05 ml aliquots of a peptone broth (containing 1% w/v polypeptone and 0.5% w/v sodium chloride) in a microtest dish (made by Falcon plastics Co.) and cultured at 37° C overnight.

One drop of a suspension (containing $5 \times 10^8$ cells/ml) of *E. coli* strain Y815, similarly cultured in the same peptone broth, was then added to each well and the mixture was cultured overnight at 30° C. This gave the opportunity for conjugation to occur between the strain of the Clark and Carbon collection and the strain Y815.

To the cultured product in each well was added one drop of crude ColEI. prepared by the method of Spadik at et al [J. Mol. Biol., 53, 49-67]and *E. coli* phage T6 (*E. coli* Sttain Y815 1S T6-resistant). and the mixture was incubated at 37° C for 30 minutes. A sample of the cultured product from each well was inoculated onto both a PT plate (peptone broth containing 8 μg/ml of tetracycline and 1% w/v agar) and a PT plate to which 0.2 mM of IPTG had been added, and the plates were then cultured at 37° C overnight. Afterwards, the plates were examined and the strain which grew t©a similar extent on both plates was selected; this was presumed to be strain Y815 but transformed by a plasmid imparting IPTG-insensitivity. The strain from the collection of Clarke and Carbon which imparted this insensitivity is that hereinbefore identified as strain SANK 71983.

EXAMPLE 2

Culture of E coli SANK 71983. preparation of plasmid pLC3-13 and transformation of strain Y815

E. coli strain SANK 71983 complementing the IPTG-sensitivity of strain Y815 was selected as described in Example 1. It appears that the strain contains a specific plasmid (plasmid pLC3-13) which was transferred to the Y815 strain by conjugation, thus rendering the Y815 strain IPTG-insensitive. In this Example, the plasmid pLC3 13 was prepared and strain Y815 was transformed by the plasmid to confirm its effect.

E. coli strain SANK 71983 was cultured in an L medium (1% w/v Bacto-triptore 0.5% w/v yeast extract, 0.5% w/v sodium chloride and 0.1% w/v glucose, adjusted to pH 7.2) at J7° C, to which was added, at the late logarithmic proliferation phase. 150μg/ml of chloramphenicol, and the mixture was cultured overnight. Cells were collected from the culture broth by low temperature centrifugation (1,000 G, 4° C, 20 minutes) and the supernatant was removed to give a cell pellet.

The cell pellet was resuspended in a 50 mM Tris-hydroxymethylaminomethane/Tris-hydrochloric acid buffer (pH 8 0) containing 20 ml of a 25% w/v aqueous solution of sucrose. 4 ml of a lysozyme solution having a concentration of 5 μg/ml were added to the suspension and the mixture was incubated at 0° C for 5 minutes. 8 ml of a 0.25 molar solution of sodium ethylenediaminetetraacerate were then added to the mixture, which was further incubated at 0° C for 5 minutes. The mixture was then vigorously stirred, whilst adding 10 ml of a 5 molar aqueous solution of sodium chloride and 4 ml of a 10% w/v aqueous solution of sodium dodecylsulfate. After this, the mixture was left to stand at 0° C for at least 3 hours, whereupon it was centrifuged at 10,000 G for 30 minutes.

The resulting supernatant was mixed with cesium chloride and then with the fluorescent agent ethidium bromide, to prepare a solution with a density of 1.620 g/cm$^3$, and this was subjected to equilibrium density gradient centrifugation at 150.000 G and 18° C for 4 hours. Ultraviolet irradiation of the centrifuged tube revealed a fluorescent band of the plasmid pLC3-13 in the shape of a closed ring beneath the fluorescenr band of linear chromosomal DNA. This plasmid fraction was sampled, the ethidium bromide was removed with buranol, and the aqueous layer was dialyzed with a buffer (10 mM Tris, 10 mM sodium chloride and 1 mM sodium ethylenediaminetetraacetate, pH 7.5) to give pure plasmid pLC3-13.

Using the plasmid pLC3-13 thus attained, E. coli strain Y815 was transformed by a conventional method (e.g. as described in "Methods of Enzymology", 68, 252, Academic press). This transformation resulted in an IPTG-insensitive strain, thus indicating that the PLP gene Was carried by plasmid pLC3-13.

This transformed strain was cultured overnight at 30° C in an M3 medium [J. Bacteriol.. 43, 661–667 (1980)] and then diluted 10-fold with 5 ml of an M9 medium (ibid.). The diluted culture product was then subjected to shaking culture at 30° C and, when the absorbance at 660 nm became 0.3. IPTG was added to a concentration of 6 mM. Culturing was then continued and, when the same absorbance reached 0.4, L-$^{35}$S-methionine was then added to a concentration of 0.5 μCi/0.1 μg/ml; the mixture was then subjected to shaking culture at 30° C for 30 minutes. At the end of this time, the bacterial cells were separated from the culture product and the membrane fraction was obtained by the method of Inoue et al [Proc. Natl. Acad. Sci.. 649, 57–61 (1969)].

This membrane fraction was examined by polyacrylamide-sodium dodecylsulfate-gel electrophoresis and fluorography and it was found that it contained a large amount of mature lipoprotein and substantially no PLP. Furthermore, when the membrane fraction was subjected to an in vitro assay of PLP signal peptidase (as described in J. Biochem., 93, 1509–1515), a high level of PLP signal peptidase was found, whilst no corresponding activity could be detected in the original E. coli strain Y815. This shows clearly that plasmid pLC3-13 donates signal peptidase activity to strain Y815.

EXAMPLE 3

Culturing of E. coli strain SANK 72083 and separation of plasmid pKD3 therefrom

E coli strain SANK 720BJ (which is E. coli strain Y8 transformed by plasmid pK03 in a conventional manner) was cultured in L medium as described in Example 2, but, since the plasmid pKD3 has the pstI fragment from plasmid pLC3 13 at the psrI site of the plasmid vector pBR322, elimination of the plasmid was prevented by incorporating tetracycline, instead of chloramphenicol, in the L medium to a final concentration of 10 μg/ml.

Plasmid pKD3 was separated from this strain in the same way as plasmid pLC3-13 was separated from strain SANK 71983 in Example 2.

EXAMPLE 4

Culture of E. coli strain SANK 72183 and separation of plasmid pHY11 therefrom

E. coli strain SANK 72I83 (the strain YB transformed by plasmid pHY11) was cultured as described in Example 2, but, since pHY11 has a tetracycline-resistant gene in its molecule, elimination to the plasmid was prevented by carrying out the culture in a L medium to which tetracycline had been added to a final concentration of 10 μ/mg, preparation of the plasmid pHY11 from this strain was then carried out as described in Example 2.

EXAMPLE 5

Culture of E. coli strain SANK 72283 and separation of plasmid pHY12 therefrom

The procedure of Example 4 was repeated, but using E. coli strain SANK 72283 (strain Y8 transformed by plasmid pHY12), to give a culture broth of E. coli strain SANK 72283. Plasmid pHY12 was prepared from this strain using the procedure described in Example 2.

EXAMPLE 6

Culture of E. coli strain SANK 72383 and separation of plasmid oKD5 therefrom

*E. coli* strain SANK 72383 (strain Y8 transformed by plasmid pKD5) was cultured following the procedure described in Example 2. except that, since plasmid pKD5 has the HindIII fragment from plasmid pLC3-13 at the HindIII site of the plasmid vector pBR322, elimination of the plasmid was prevented by culturing the strain in an L medium to which amplcillin was added to a final concentration of 10 μg/ml.

Preparation of plasmid pKD5 from this strain was carried out following the procedure described in Example 2.

We claim:

1. An isolated and purified DNA sequence coding for the prolipoprotein signal peptidase of *E. coli* and wherein said sequence is separate from the native *E. coli* chromosome and its native *E. coli* plasmid.

2. A sequence as claimed in claim 1, comprising a 4.3kb fragment preparable by digestion of plasmid LC3-13 with the restriction enzyme AccI.

3. A sequence as claimed in claim 1, comprising the cleavage positions: 0.7kb for PvuII, 1.7kb for BglII, 1.9kb for KpnI, 2.1kb for pstI, 2.2kb for BamHI, 2.4kb for MluI, 3.5kb for StuI and 4.3kb for AccI, measuring from the cleavage position of AccI.

4. A recombinant DNA comprising a DNA sequence as defined in any one of claims 1 to 3, incorporated in a vector DNA.

5. A recombinant DNA as claimed in claim 4, in which said vector DNA is a plasmid selected from pBR322 and pHY001.

6. An isolated and purified plasmid pLC3-13 separate from its native *E. coli* strain.

7. An isolated and purified plasmid pKD3.

8. An isolated and purified plasmid pHY11.

9. An isolated and purified plasmid pHY12.

10. An isolated and purified plasmid pKD5.

11. A microorganism transformed by a recombinant DNA as claimed in claim 4.

12. A microorganism transformed by a recombinant DNA as claimed in claim 5.

13. A microorganism transformed by a plasmid as claimed in any one of claims 6, 7, 8, 9 or 10.

14. A microorganism as claimed in claim 13, wherein said microorganism is a strain of *E. coli*.

15. A microorganism selected from the group consisting of *E. coli* strains SANK 72083, SANK 72183, SANK 72283 and SANK 72383.

* * * * *